(12) United States Patent
Wei et al.

(10) Patent No.: US 12,019,232 B2
(45) Date of Patent: Jun. 25, 2024

(54) ENDOSCOPE LENS, CAMERA MODULE AND ENDOSCOPE

(71) Applicant: JIANGXI LIANCHUANG ELECTRONIC CO., LTD., Nanchang (CN)

(72) Inventors: Wenzhe Wei, Nanchang (CN); Xuming Liu, Nanchang (CN); Jiyong Zeng, Nanchang (CN); Zhuo Wang, Nanchang (CN)

(73) Assignee: JIANGXI LIANCHUANG ELECTRONIC CO., LTD., Nanchang (CN)

( * ) Notice: Subject to any disclaimer, the term of this patent is extended or adjusted under 35 U.S.C. 154(b) by 262 days.

(21) Appl. No.: 17/521,819

(22) Filed: Nov. 8, 2021

(65) Prior Publication Data
US 2022/0066193 A1 Mar. 3, 2022

Related U.S. Application Data

(63) Continuation-in-part of application No. PCT/CN2020/085923, filed on Apr. 21, 2020.

(30) Foreign Application Priority Data

Jun. 14, 2019 (CN) .......................... 201910516654.2

(51) Int. Cl.
*G02B 23/24* (2006.01)
*A61B 1/00* (2006.01)
(Continued)

(52) U.S. Cl.
CPC ........ *G02B 23/243* (2013.01); *A61B 1/00186* (2013.01); *G02B 13/003* (2013.01); *G02B 9/04* (2013.01)

(58) Field of Classification Search
CPC ...... G02B 23/243; G02B 13/003; G02B 9/04; A61B 1/00186; A61B 1/00096; A61B 1/05; A61B 1/00071
See application file for complete search history.

(56) References Cited

U.S. PATENT DOCUMENTS

| | | | | |
|---|---|---|---|---|
| 6,476,851 B1 * | 11/2002 | Nakamura | ......... | A61B 1/00096 348/340 |
| 2003/0210341 A1 * | 11/2003 | Isono | ....................... | G02B 9/56 348/335 |

(Continued)

FOREIGN PATENT DOCUMENTS

| CN | 103502869 A | 1/2014 |
|---|---|---|
| CN | 103890631 A | 6/2014 |

(Continued)

OTHER PUBLICATIONS

WIPO, International Search Report for PCT Application No. PCT/CN2020/085923, Jul. 1, 2020.
(Continued)

*Primary Examiner* — Michael E Teitelbaum (57) ABSTRACT

Provided is an endoscope lens, a camera module and an endoscope. From an object side to an image side, the endoscope lens sequentially includes: a first lens having a concave object side surface and a convex image side surface; a second lens with a positive or negative refractive power; and a filter arranged between the second lens and the image side. Each of the first lens and the second lens is a glass or plastic aspheric lens. The endoscope lens further includes a stop positioned between the first lens and the object side or between the first lens and the second lens.

17 Claims, 11 Drawing Sheets

(51) Int. Cl.
*G02B 9/04* (2006.01)
*G02B 13/00* (2006.01)

(56) References Cited

U.S. PATENT DOCUMENTS

| | | | | |
|---|---|---|---|---|
| 2009/0185294 A1* | 7/2009 | Teraoka | ............... | G02B 13/003 |
| | | | | 359/794 |
| 2014/0376112 A1* | 12/2014 | Tsai | ..................... | G02B 13/003 |
| | | | | 359/717 |
| 2018/0132700 A1* | 5/2018 | Ouyang | ............. | A61B 1/00052 |

FOREIGN PATENT DOCUMENTS

| | | | |
|---|---|---|---|
| CN | 104471460 A | | 3/2015 |
| CN | 204363936 U | | 6/2015 |
| CN | 107045195 A | | 8/2017 |
| CN | 107544127 A | * | 1/2018 |
| CN | 108139567 A | | 6/2018 |
| CN | 108873311 A | | 11/2018 |
| JP | 08286128 A | | 11/1996 |
| JP | 09325285 A | | 12/1997 |
| JP | 2006243092 A | | 9/2006 |
| JP | 2018055059 A | | 4/2018 |

OTHER PUBLICATIONS

SIPO, First Office Action for CN Application No. 201910516654.2, Feb. 1, 2021.
SIPO, Office Action issued for CN Application No. 201910516654.2, Mar. 16, 2021.
Written Opinion of the International Search Authority in corresponding International application No. PCT/CN2020/085923.

* cited by examiner

ENDOSCOPE LENS, CAMERA MODULE AND ENDOSCOPE

CROSS-REFERENCE TO RELATED APPLICATION

This application is a continuation-in-part of PCT Application PCT/CN2020/085923, filed on Apr. 21, 2020. The PCT Application claims priority to a Chinese patent application No. 201910516654.2 filed on Jun. 14, 2019. The contents of the aforementioned applications are incorporated herein by reference.

TECHNICAL FIELD

The disclosure relates to the technical field of medical lenses, and particularly to an endoscope lens, a camera module and an endoscope.

BACKGROUND

An endoscope is a medical device that penetrates into the human body through natural channels of the human body, and enables the internal structure or pathological conditions to be observed through captured images. At present, most endoscopes have a large diameter, which causes the process of entering the human body to be painful for the subject, and makes it is difficult to inspect lesion parts located a narrow channel.

Further, the related endoscope lens also has defects of large diameter, shadow depth of field, and narrow field of view. The smaller the diameter of the endoscope, the less discomfort caused to the human body. In contrast, the excessive diameter of the endoscope will cause the production cost to be increased. Also, the field of view and the depth of field are also important parameters for the endoscope, in which a narrow field of view affects the observed range of the endoscope lens, and a shadow depth of field affects the observed depth of the endoscope lens.

SUMMARY

In view of the above, embodiments of the present disclosure aims to provide an endoscope lens that has a reduced diameter, a wide field of view, and a large depth of field.

An endoscope lens, from an object side to an image side thereof, sequentially including:
  a first lens having a concave object side surface and a convex image side surface;
  a second lens with a positive or negative refractive power; and
  a filter arranged between the second lens and the image side;
  where each of the first lens and the second lens is a glass or plastic aspheric lens; and
  where the endoscope lens further includes a stop arranged between the first lens and the object side or between the first lens and the second lens.

The embodiments of the disclosure further discloses a camera module, which includes the endoscope lens as mentioned above, and an image sensor opposite to the endoscope lens.

The embodiments of the disclosure further provide an endoscope, which includes the camera module as mentioned above, a processor, and a memory. The camera module is configured to capture images. The processor is configured to process the captured images. The memory is configured to store the captured images.

BRIEF DESCRIPTION OF THE DRAWINGS

The above-mentioned and/or additional aspects and advantages of the present disclosure will become obvious and well understood from the following description of the embodiments in conjunction with the drawings, in which.

DETAILED DESCRIPTION OF PREFERRED EMBODIMENTS

In order to make the objectives, features, and advantages of the present disclosure more obvious and understandable, the specific embodiments of the present disclosure will be described in detail below with reference to the drawings. Several embodiments of the disclosure are shown in the drawings. However, the present disclosure can be implemented in many different forms and is not limited to the embodiments described herein. Rather, the purpose of providing these embodiments is only to make the present disclosure more thorough and comprehensive.

Unless otherwise defined, all technical and scientific terms used herein have the same meaning as commonly understood by those skilled in the technical field of the present disclosure. The terms used in the description of the present disclosure herein are only for the purpose of describing the specific embodiments, and are not intended to limit the present disclosure. The term "and/or" used herein includes any and all combinations of one or more listed items.

The embodiments of present disclosure provide an endoscope lens. From an object side to an image side, the endoscope lens sequentially includes:

a first lens having a concave object side surface and a convex image side surface;

a second lens with a positive or negative refractive power: and a filter arranged between the second lens and the image side;

where the first lens is a glass or plastic aspheric lens, and the second lens is a glass or plastic aspheric lens: and the endoscope lens further includes a stop, and the stop is arranged between the first lens and the object side or between the first lens and the second lens.

In some embodiments, in order to effectively reduce the size of the endoscope lens, the endoscope lens meets expressions:

$r1/r2 > 1$:

$TTL/D_{max} < 3$;

where r1 represents a radius of curvature of the object side surface of the first lens, r2 represents a radius of curvature of the image side surface of the first lens, TTL represents an optical total length of the endoscope lens, and $D_{max}$ represents a diameter of the largest one of the lenses in the endoscope lens.

The radius of curvature of the object side surface of the first lens has a same sign as the radius of curvature of the image side surface of the first lens. Accordingly, the first lens is a meniscus lens. This enables the ratio of the optical total length to the maximum diameter to be reduced. In this way, the diameter and the optical total length of the endoscope lens can be effectively reduced, while ensuring a sufficiently wide field of view of the endoscope lens. In particular, the diameter of the endoscope lens can be ensured to be less than or equal to 1.0 mm, and the optical total length of the endoscope lens can be ensured to be no more than 2.0 mm. This can effectively alleviate the patient's pain during physical examination, and can enable the endoscope lens to access a narrow lesion part for examination.

In some embodiments, in order to ensure a large depth of field of the endoscope lens, and thus increase the observed depth, the endoscope lens meets an expression:

$0 < (f^2/Fno) + f < 1$:

where f represents an effective focal length of the endoscope lens, and Fno represents an F number of the endoscope lens.

When this expression is met, the endoscope lens can be ensured to have a sufficiently large range of depth of field, and a clear image can be obtained by the endoscope lens provided by the embodiments of the invention within a range of depth of field from 5 mm to 35 mm. This increases the examination range and ensures a sufficient observed depth in the medical examination.

In some embodiments, in order to enable the endoscope lens to well suppress the distortions and thus reduce the imaging deformation caused by the distortions, the endoscope lens meets an expression:

$0 \text{ mm}/° < IH/\theta < 0.01 \text{ mm}/°$:

where θ represents half of the field of view of the endoscope lens, and IH represents an actual image height of the endoscope lens at the half of the field of view θ.

By suppressing the f-θ) distortion, the magnification at the edge of the field of view is increased, thereby improving the resolving power at the edge of the endoscope lens. Accordingly, the part of image obtained at the edge of the field of view has a sufficient resolution, after being flattened and expanded.

In some embodiments, both the first lens and the second lens are aspheric lenses.

The aspheric lenses can not only enable various aberrations, such as spherical aberration, coma, field curvature and distortion, to be effectively corrected, but also enable the number and the diameters of the lenses to be effectively reduced, facilitating reduction of the overall size of the endoscope lens.

In some embodiments, the surface shape of each of the aspheric lenses of the endoscope lens meets an expression:

$$z = \frac{ch^2}{1 + \sqrt{1-(1+K)c^2h^2}} + Bh^4 + Ch^6 + Dh^8 + Eh^{10} + Fh^{12};$$

where z represents a distance between a point on a curved surface and a vertex of the curved surface along an optical axis, c represents a curvature of the vertex of the curved surface, K represents a quadratic surface coefficient, h represents a distance between the point on the curved surface and the optical axis, B represents a fourth order surface coefficient, C represents a sixth order surface coefficient, D represents an eighth order surface coefficient, E represents a tenth order surface coefficient, and F represents a twelfth order surface coefficient.

Further, the optical total length of the endoscope lens is less than 1.50 mm.

Further, the field of view of the endoscope lens is greater than or equal to 120°.

Further, the endoscope lens can be applied in a spectral range of 400 nm to 700 nm.

In the above-mentioned endoscope lens, the first lens is configured to collect light and correct distortions, and enable the diameter of the endoscope lens to be effectively reduced. The second lens is mainly configured to eliminate aberrations, such as spherical aberration, field curvature, and astigmatism. By means of the reasonable arrangement and coordination of the individual lenses, the filter and the stop, the diameter of the endoscope lens can be reduced while ensuring a wide field of view. The diameter of the endoscope lens can be reduced to be no more than 1.0 mm, and the optical total length of the endoscope lens can be less than or equal to 2.0 mm. This can effectively relieve the patient's pain during physical examination, and can enable the endoscope lens to access a narrow lesion part for examination. Further, the field of view of the endoscope lens can be ensured to be greater than or equal to 120°, and a clear image can be obtained within a range of depth of field from 5 mm to 35 mm. This enables the endoscope lens to have a small diameter, a large depth of field, and a wide field of view, effectively increasing the observed range and the observed depth. In addition, the endoscope lens also has small distortion, which improves the resolving power at the edge and ensures the imaging effect.

The present disclosure will be further described in several embodiments below. The following embodiments just illustrate preferred implementations of the present disclosure. However, the implementations of the present disclosure are not limited only by the following embodiments, and any other variations, substitutions, combinations or simplifications, that are made without departing from the concept of the present disclosure, should be regarded as equivalent implementations, and fall within the protection scope of the present disclosure.

In the following embodiments, the thickness and the radius of curvature of the individual lenses in the endoscope lens are different. For specific differences, the parameter tables of the embodiments may be referred to.

Embodiment 1

Figure 1:
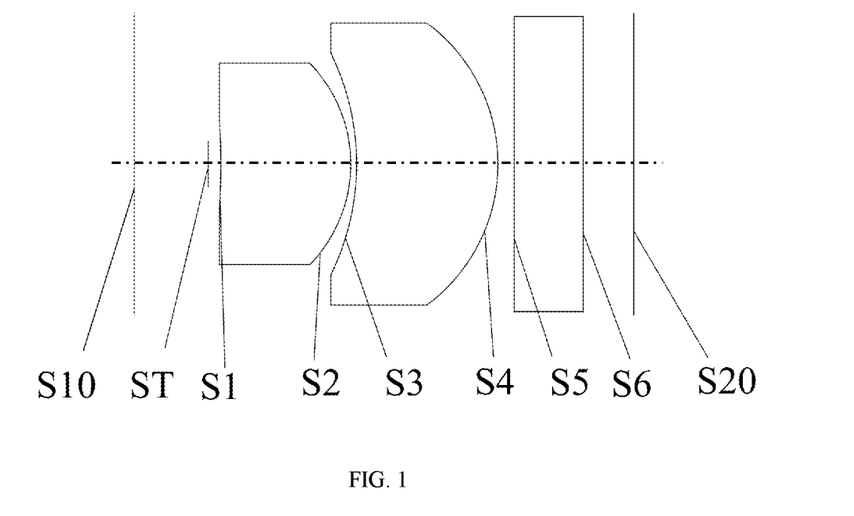
FIG. 1 is a schematic cross-section view illustrating a structure of an endoscope lens provided by a first embodiment of the present disclosure.

Referring to FIG. 1, the structure of an endoscope lens 100 provided by the first embodiment of the present disclosure is illustrated. From an object plane S10 to an image plane S20, the endoscope lens sequentially includes: a stop ST, a first lens L1, a second lens L2, and a filter G1.

The first lens L1 has a positive refractive power. The object side surface S1 of the first lens L1 is concave, and the image side surface S2 of the first lens L1 is convex. The first lens L1 is a glass aspheric lens.

The second lens L2 has a positive refractive power. The object side surface S3 of the second lens L2 is concave, and the image side surface S4 of the second lens L2 is convex. The second lens L2 is a glass aspheric lens. In other embodiments of the present disclosure, the second lens L2 may be a plastic aspheric lens. The object side surface S3 of the second lens L2 has a central concave portion and a flat portion surrounds the concave portion. The diameter of the second lens L2 is larger than the diameter of the first lens L1.

The stop ST is provided in front of the first lens L1 (that is, between the first lens L1 and the object plane S10). The filter G1 is provided between the second lens L2 and the image plane S20. The object side surface of the filter G1 is S5, and the image side surface of the filter G1 is S6. The distance between the second lens L2 and the filter G1 is smaller than the distance between the filter G1 and the image plane S20, along the optical axis (as indicated by the dashed line). The diameter of the stop ST is smaller than the diameter of the first lens L1, and smaller than the diameter of the second lens L2. The relevant parameters of each lens in the endoscope lens 100 provided in the first embodiment of the present disclosure are shown in Table 1-1.

TABLE 1-1

| Surface No. | Surface type | Radius of curvature | Thickness | Refractive index | Abbe number |
|---|---|---|---|---|---|
| S10 | Object plane | Infinity | 10.000000 | | |
| ST | Stop | Infinity | 0.039083 | | |
| S1 | Aspheric surface | −5.518499 | 0.396347 | 1.851 | 40.10 |
| S2 | Aspheric surface | −0.360885 | 0.017873 | | |
| S3 | Aspheric surface | −0.458848 | 0.430578 | 1.851 | 40.10 |
| S4 | Aspheric surface | −0.352798 | 0.050000 | | |
| S5 | Spherical surface | Infinity | 0.210000 | 1.517 | 64.21 |
| S6 | Spherical surface | Infinity | 0.153863 | | |
| S20 | Image plane | Infinity | — | | |

The parameters of the aspheric surfaces of the individual aspheric lenses in this embodiment are shown in Tables 1-2A and 1-2B.

TABLE 1-2A

| Surface No. | K | B | C |
|---|---|---|---|
| S1 | 49.999098 | −4.847456E+00 | −5.071720E+02 |
| S2 | −6.805635 | −3.738569E+00 | −3.711547E+01 |
| S3 | −12.258980 | 2.788590E−02 | −4.457130E+01 |
| S4 | −2.872556 | −1.765773E+00 | −4.579382E+00 |

TABLE 1-2B

| Surface No. | D | E | F |
|---|---|---|---|
| S1 | 1.289472E+04 | 1.843671E+05 | −1.876634E+07 |
| S2 | 4.236333E+02 | −4.888397E+03 | 3.204418E+04 |
| S3 | 2.147507E+02 | 1.747330E+03 | −6.953613E+03 |
| S4 | 1.409523E+02 | −9.421510E+02 | 2.257683E+03 |

Figure 2:
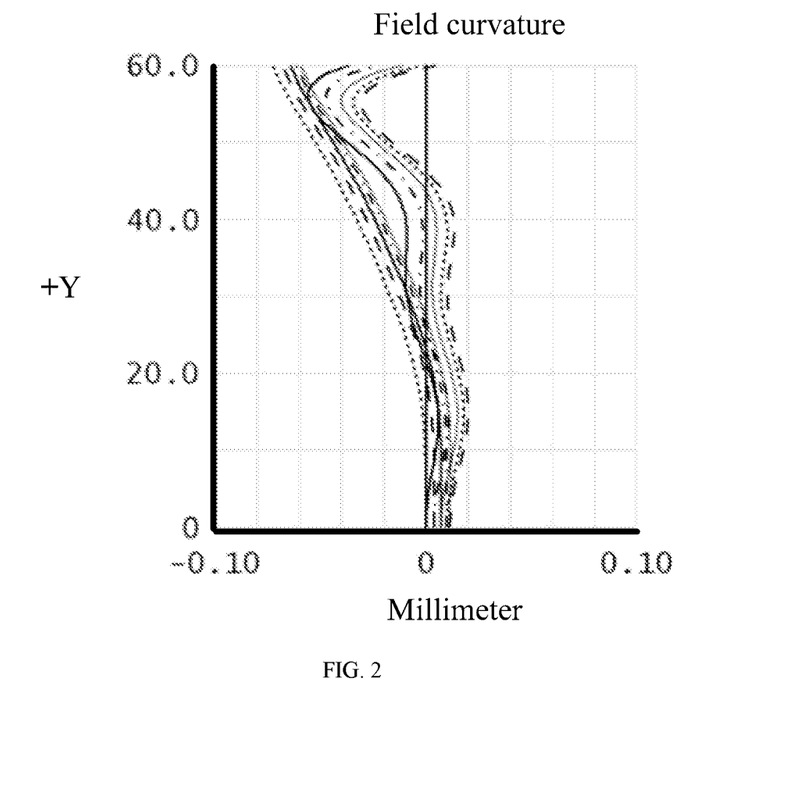
FIG. 2 is a diagram illustrating field curves of the endoscope lens provided by the first embodiment of the present disclosure.
Figure 3:
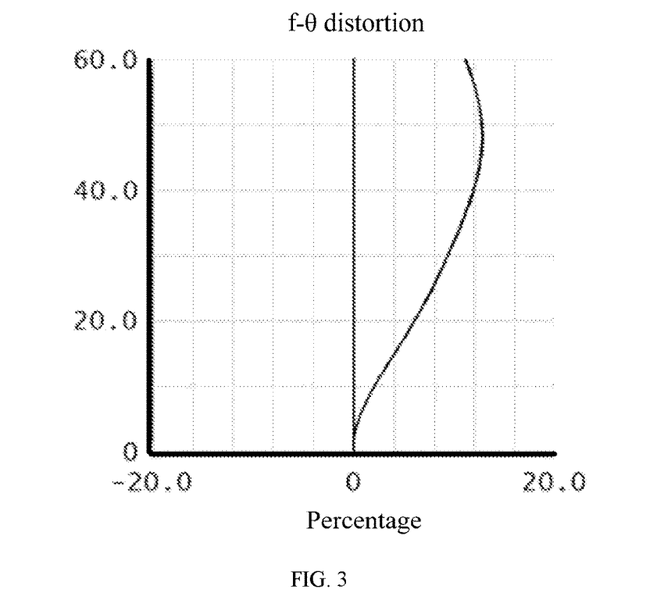
FIG. 3 is a diagram illustrating a distortion curve of the endoscope lens provided by the first embodiment of the present disclosure.
Figure 4:
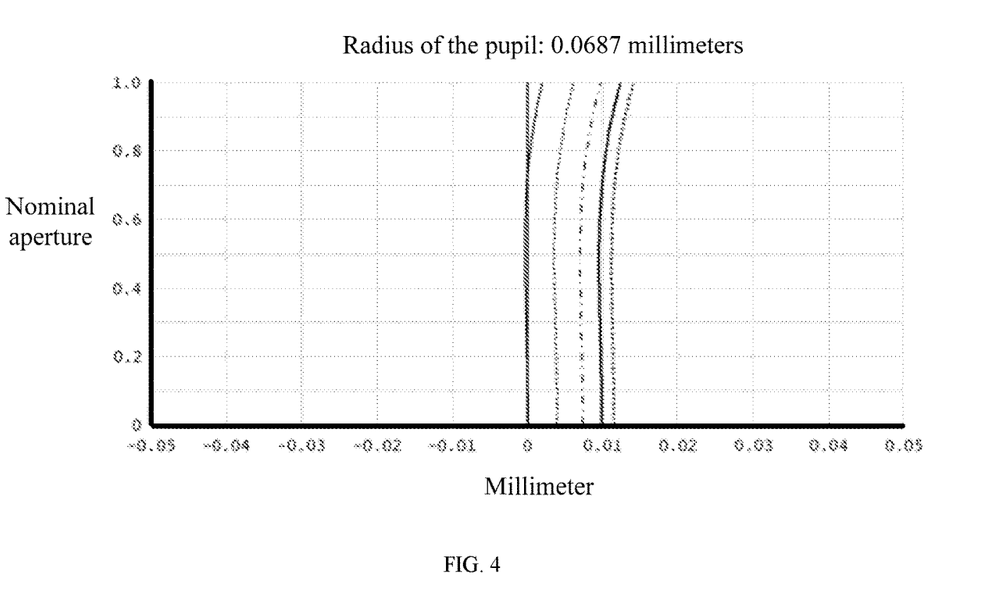
FIG. 4 is a diagram illustrating axial chromatic aberration curves of the endoscope lens provided by the first embodiment of the present disclosure.

In this embodiment, the field curvatures, distortions and axial chromatic aberrations thereof are shown in FIG. 2, FIG. 3 and FIG. 4, respectively. It can be seen from FIG. 2 to FIG. 4 that the field curvatures, distortions, and chromatic aberrations can all be well corrected in this embodiment. It should be noted that, there are multiple curves in FIG. 2 and FIG. 4, in which different solid lines or dashed lines correspond to different wavelengths.

Embodiment 2

Figure 5:
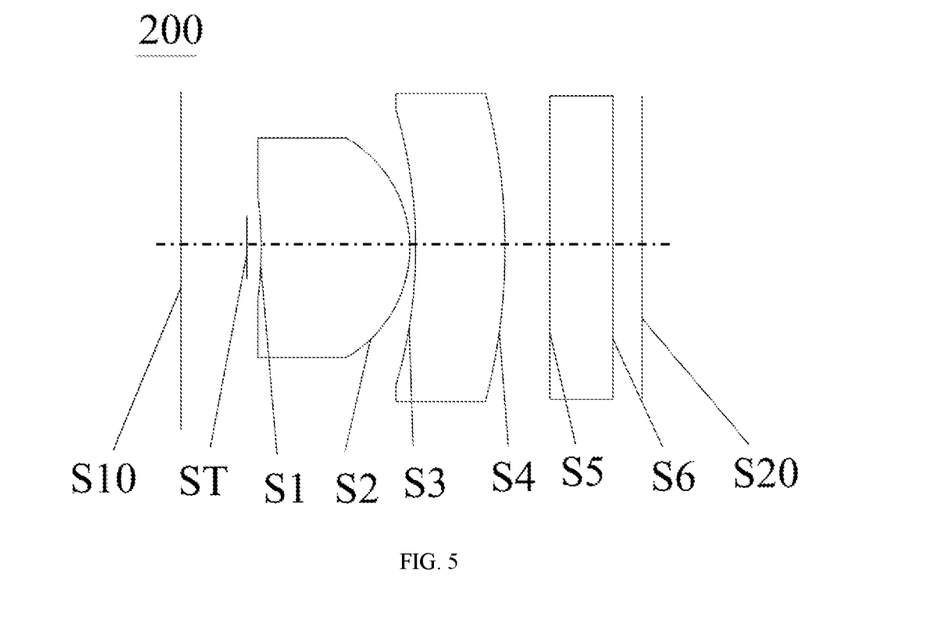
FIG. 5 is a schematic cross-section view illustrating a structure of an endoscope lens provided by a second embodiment of the present disclosure.

Referring to FIG. 5, the structure of an endoscope lens 200 provided by a second embodiment of the present disclosure is illustrated. The endoscope lens 200 in this embodiment is substantially the same as the endoscope lens 100 in the first embodiment, except that: in this embodiment, the second lens L2 of the endoscope lens 200 is a plastic aspheric lens and has a negative refractive power, and the radius of curvature and material of each lens are selected differently. The specific parameters of the individual lenses are shown in Table 2-1. In this embodiment, a center thickness of the first lens L1 is larger than a center thickness of the second lens L2.

TABLE 2-1

| Surface No. | Surface type | Radius of curvature | Thickness | Refractive index | Abbe number |
|---|---|---|---|---|---|
| S10 | Object plane | Infinity | 10.000000 | | |
| ST | Stop | Infinity | 0.047714 | | |
| S1 | Aspheric surface | −1.976923 | 0.496712 | 1.851 | 40.10 |
| S2 | Aspheric surface | −0.380989 | 0.019344 | | |
| S3 | Aspheric surface | 3.204712 | 0.299125 | 1.545 | 56.00 |
| S4 | Aspheric surface | 0.646387 | 0.150000 | | |
| S5 | Spherical surface | Infinity | 0.210000 | 1.517 | 64.21 |
| S6 | Spherical surface | Infinity | 0.098817 | | |
| S20 | Image plane | Infinity | — | | |

The parameters of the aspheric surfaces of the individual aspheric lenses in this embodiment are shown in Tables 2-2A and 2-2B.

TABLE 2-2A

| Surface No. | K | B | C |
|---|---|---|---|
| S1 | 27.759809 | −4.360434E−01 | −4.835128E+02 |
| S2 | −2.351084 | −3.402961E+00 | −4.121543E+01 |
| S3 | 45.062240 | −1.409672E+00 | −5.634296E+01 |
| S4 | 0.449844 | −2.344056E+00 | −3.254907E+01 |

TABLE 2-2B

| Surface No. | D | E | F |
|---|---|---|---|
| S1 | 1.220048E+04 | 3.278592E+05 | −1.054969E+07 |
| S2 | 6.270839E+02 | −5.692451E+03 | 2.306126E+04 |
| S3 | 1.278780E+02 | 1.645103E+03 | −5.311689E+03 |
| S4 | 1.535844E+02 | −3.386175E+02 | 2.060710E+02 |

Figure 6:
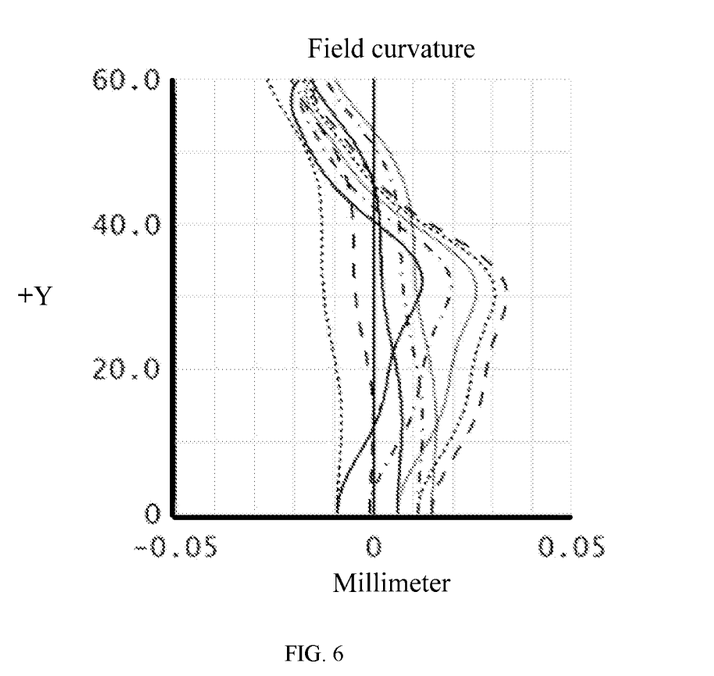
FIG. 6 is a diagram illustrating field curves of the endoscope lens provided by the second embodiment of the present disclosure.
Figure 7:
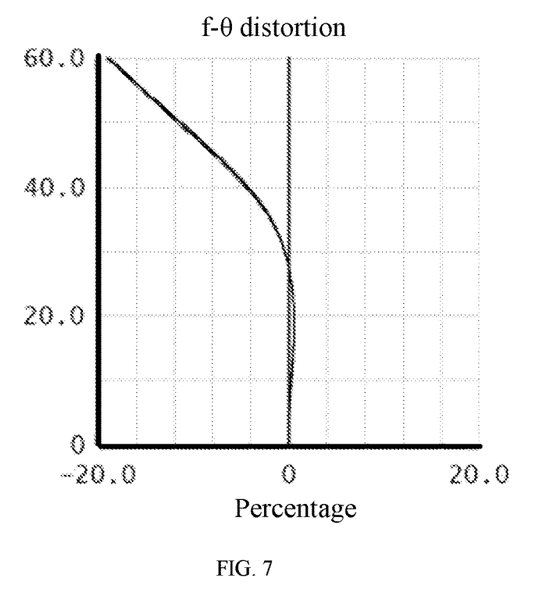
FIG. 7 is a diagram illustrating a distortion curve of the endoscope lens provided by the second embodiment of the present disclosure.
Figure 8:
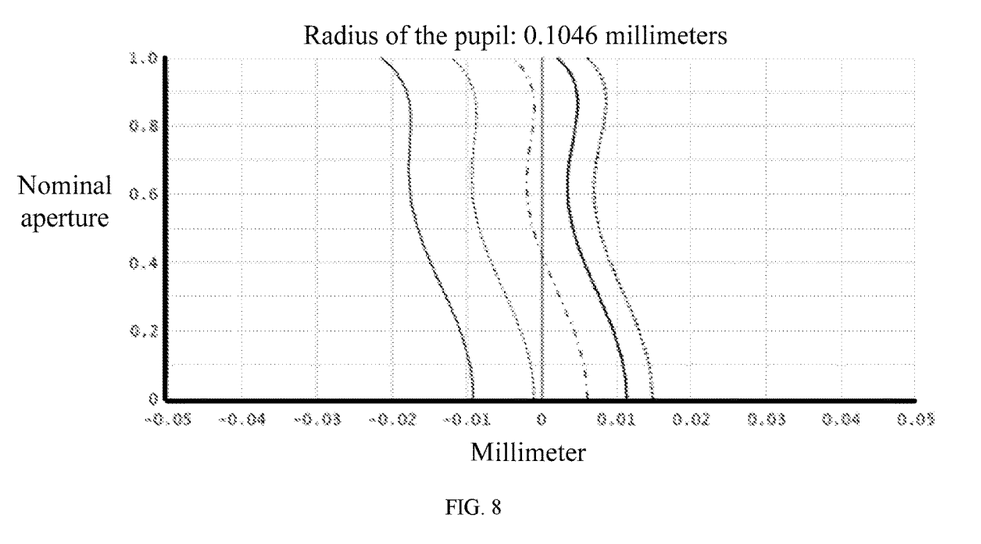
FIG. 8 is a diagram illustrating axial chromatic aberration curves of the endoscope lens provided by the second embodiment of the present disclosure.

In this embodiment, the field curvatures, distortions and axial chromatic aberrations thereof are shown in FIG. 6, FIG. 7 and FIG. 8, respectively. It can be seen from FIG. 6 to FIG. 8 that the field curvatures, distortions, and chromatic aberrations can all be well corrected in this embodiment. It should be noted that, there are multiple curves in FIG. 6 and FIG. 8, in which different solid lines or dashed lines correspond to different wavelengths.

Embodiment 3

Figure 9:
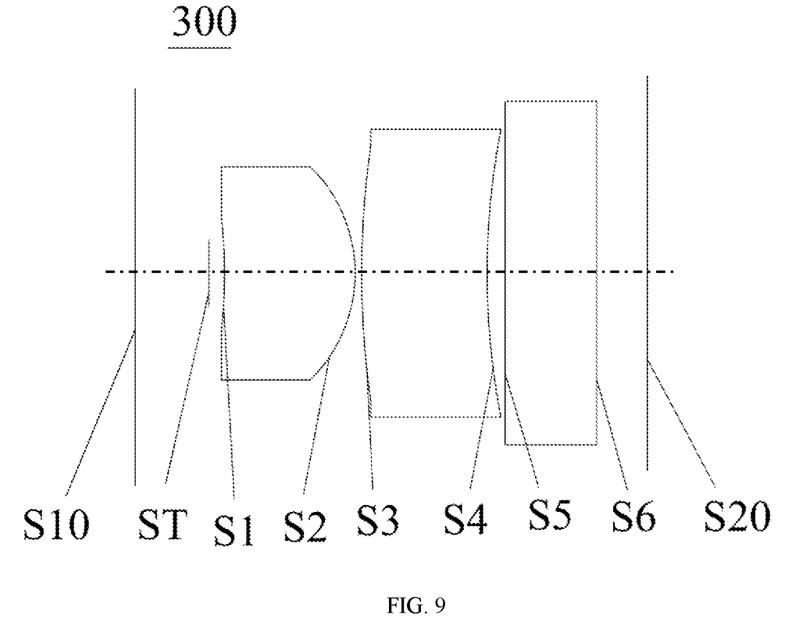
FIG. 9 is a schematic cross-section view illustrating a structure of an endoscope lens provided by a third embodiment of the present disclosure.

Referring to FIG. 9, the structure of an endoscope lens 300 provided by a third embodiment of the present disclosure is illustrated. The endoscope lens 300 in this embodiment is substantially the same as the endoscope lens 100 in the first embodiment, except that: in this embodiment, the object side surface S3 of the second lens L2 of the endoscope lens 300 is convex, the image side surface S4 of the second lens L2 is concave, and the radius of curvature and material of each lens are selected differently. The specific parameters of the individual lenses are shown in Table 3-1.

TABLE 3-1

| Surface No. | Surface type | Radius of curvature | Thickness | Refractive index | Abbe number |
|---|---|---|---|---|---|
| S10 | Object plane | Infinity | 10.000000 | | |
| ST | Stop | Infinity | 0.036238 | | |
| S1 | Aspheric surface | −1.390305 | 0.299434 | 1.851 | 40.10 |
| S2 | Aspheric surface | −0.337879 | 0.014941 | | |
| S3 | Aspheric surface | 3.694320 | 0.287934 | 1.693 | 53.20 |
| S4 | Aspheric surface | 10.089118 | 0.041400 | | |
| S5 | Spherical surface | Infinity | 0.210000 | 1.517 | 64.21 |
| S6 | Spherical surface | Infinity | 0.116526 | | |
| S20 | Image plane | Infinity | — | | |

The parameters of the aspheric surfaces of the individual aspheric lenses in this embodiment are shown in Tables 3-2A and 3-2B.

TABLE 3-2A

| Surface No. | K | B | C |
|---|---|---|---|
| S1 | −30.502214 | −7.947864E+00 | −6.079160E+02 |
| S2 | −5.238409 | −1.488791E+01 | 5.136952E+01 |
| S3 | 49.997994 | 1.455697E+00 | −4.348394E+00 |
| S4 | −40.511618 | 4.789144E+00 | −2.593538E+01 |

TABLE 3-2B

| Surface No. | D | E | F |
|---|---|---|---|
| S1 | 2.362574E+04 | 2.007734E+06 | −3.456522E+07 |
| S2 | 2.634288E+03 | −8.192043E+04 | 7.104203E+05 |
| S3 | −4.864979E+01 | 9.608992E+01 | 4.749488E+03 |
| S4 | −2.827323E+01 | 2.818327E+02 | 1.520219E+03 |

Figure 10:
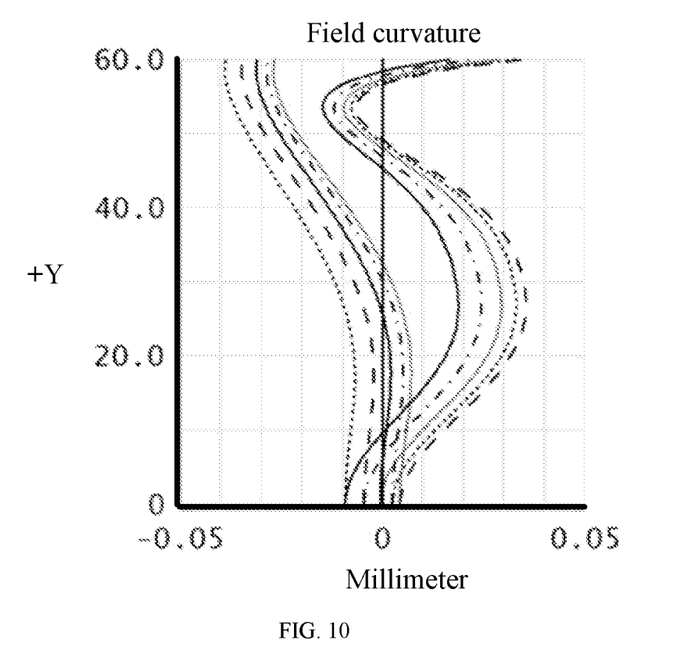
FIG. 10 is a diagram illustrating field curves of the endoscope lens provided by the third embodiment of the present disclosure.
Figure 11:
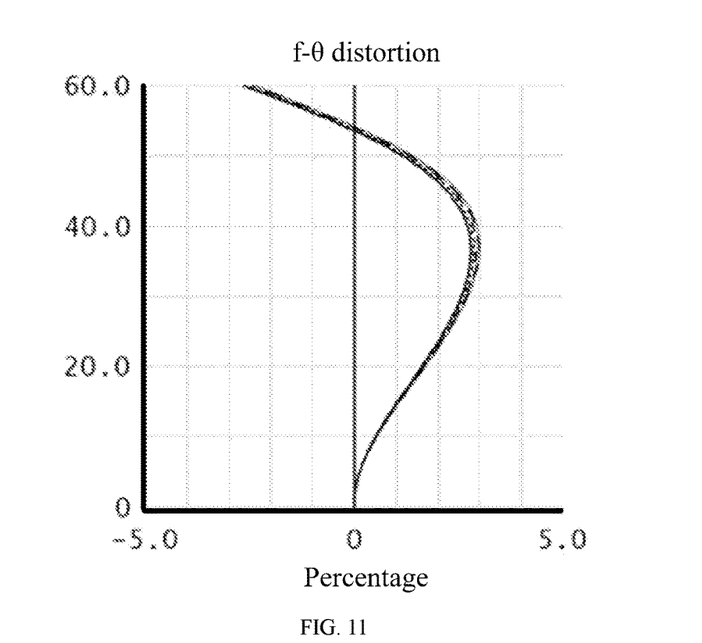
FIG. 11 a diagram illustrating a distortion curve of the endoscope lens provided by the third embodiment of the present disclosure.
Figure 12:
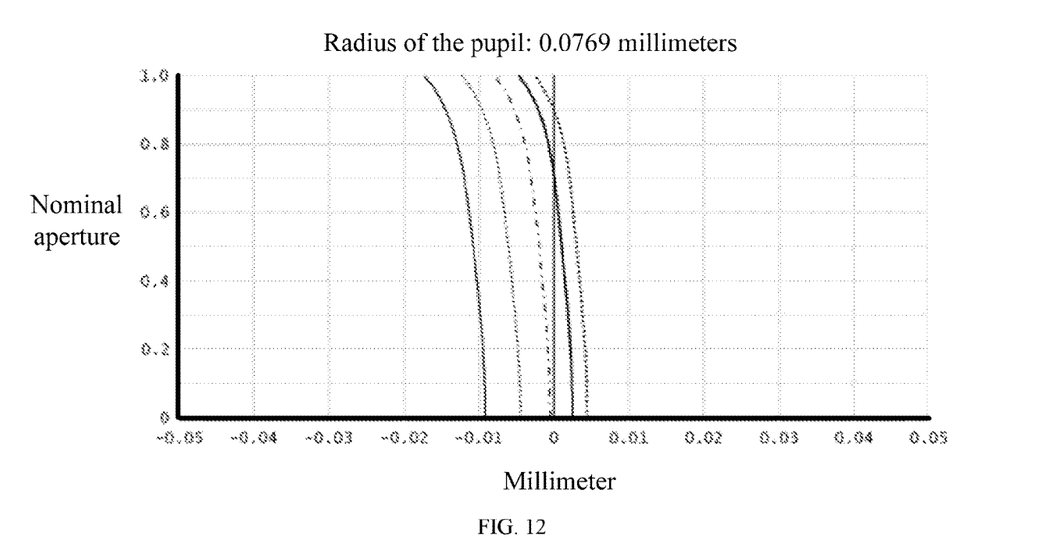
FIG. 12 is a diagram illustrating axial chromatic aberration curves of the endoscope lens provided by the third embodiment of the present disclosure.

In this embodiment, the field curvatures, distortions and axial chromatic aberrations thereof are shown in FIG. 10, FIG. 11 and FIG. 12, respectively. It can be seen from FIG. 10 to FIG. 12 that the field curvatures, distortions, and chromatic aberrations can all be well corrected in this embodiment. It should be noted that, there are multiple curves in FIG. 10 and FIG. 12, in which different solid lines or dashed lines correspond to different wavelengths.

Embodiment 4

Figure 13:
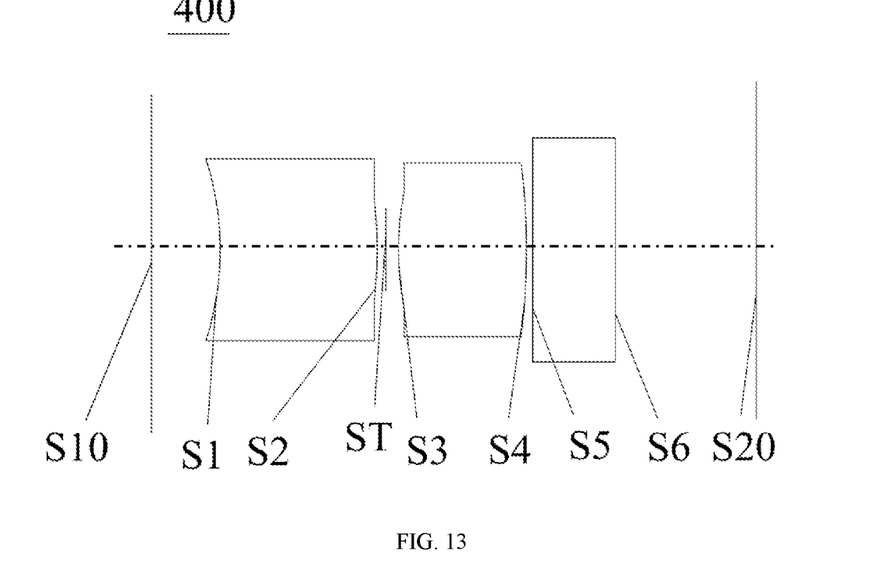
FIG. 13 is a schematic cross-section view illustrating a structure of an endoscope lens provided by a fourth embodiment of the present disclosure.

Referring to FIG. 13, the structure of an endoscope lens 400 provided by a fourth embodiment of the present disclosure is illustrated. The endoscope lens 400 in this embodiment is substantially the same as the endoscope lens 100 in the first embodiment, except that: in this embodiment, the first lens L1 of the endoscope lens 400 has a negative refractive power, the object side surface S3 of the second lens L2 is convex, the stop ST is disposed between the first lens L1 and the second lens L2, and the radius of curvature and material of each lens are selected differently. The specific parameters of the individual lenses are shown in Table 4-1.

TABLE 4-1

| Surface No. | Surface type | Radius of curvature | Thickness | Refractive index | Abbe number |
|---|---|---|---|---|---|
| S10 | Object plane | Infinity | 10.000000 | | |
| S1 | Aspheric surface | −0.734052 | 0.298056 | 1.851 | 40.10 |
| S2 | Aspheric surface | −0.577969 | 0.016642 | | |
| ST | Stop | Infinity | 0.023595 | | |
| S3 | Aspheric surface | 0.545348 | 0.243316 | 1.851 | 40.10 |
| S4 | Aspheric surface | −0.936002 | 0.011182 | | |
| S5 | Spherical surface | Infinity | 0.157136 | 1.517 | 64.21 |
| S6 | Spherical surface | Infinity | 0.269081 | | |
| S20 | Image plane | Infinity | — | | |

The parameters of the aspheric surfaces of the individual aspheric lenses in this embodiment are shown in Tables 4-2A and 4-2B.

TABLE 4-2A

| Surface No. | K | B | C |
|---|---|---|---|
| S1 | 1.763972 | 2.411778E+00 | 3.705259E+03 |
| S2 | −7.236292 | 1.398744E+00 | −7.730640E+01 |
| S3 | −50.000001 | 2.411778E+00 | 3.705259E+03 |
| S4 | −40.231738 | 1.398744E+00 | −7.730640E+01 |

TABLE 4-2B

| Surface No. | D | E | F |
|---|---|---|---|
| S1 | −2.320943E+05 | 1.445864E+06 | 8.219679E+07 |
| S2 | 1.885538E+03 | 2.747485E+05 | −8.617232E+06 |
| S3 | −2.320943E+05 | 1.445864E+06 | 8.219679E+07 |
| S4 | 1.885538E+03 | 2.747485E+05 | −8.617232E+06 |

Figure 14:
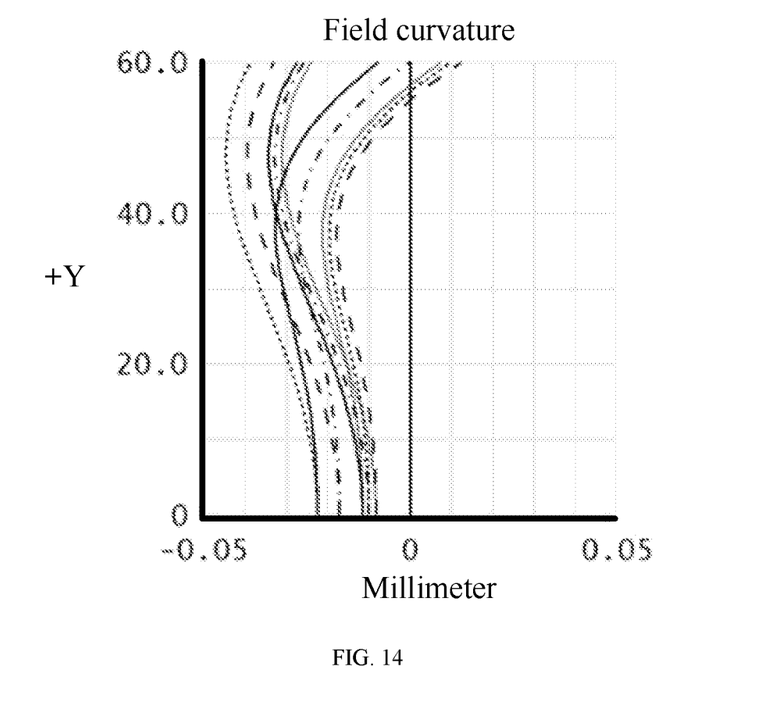
FIG. 14 is a diagram illustrating field curves of the endoscope lens provided by the fourth embodiment of the present disclosure.
Figure 15:
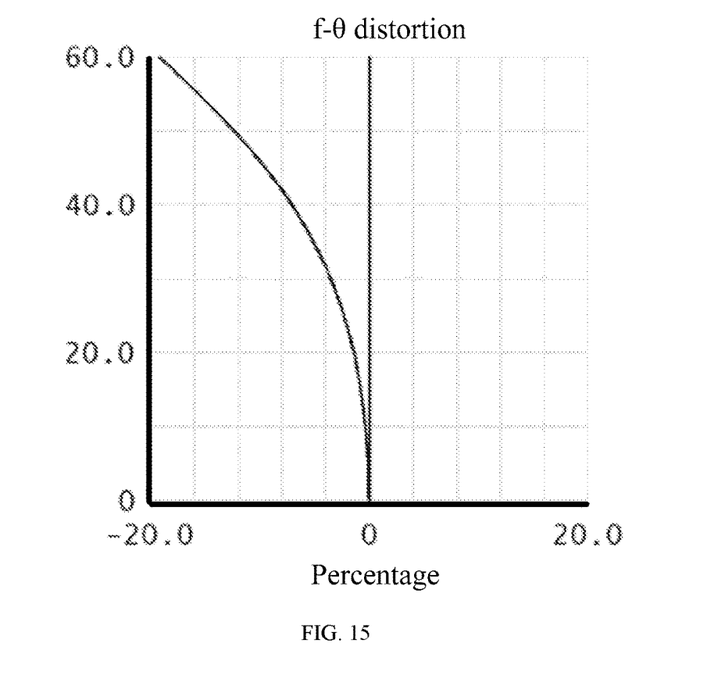
FIG. 15 is a diagram illustrating a distortion curve of the endoscope lens provided by the fourth embodiment of the present disclosure.
Figure 16:
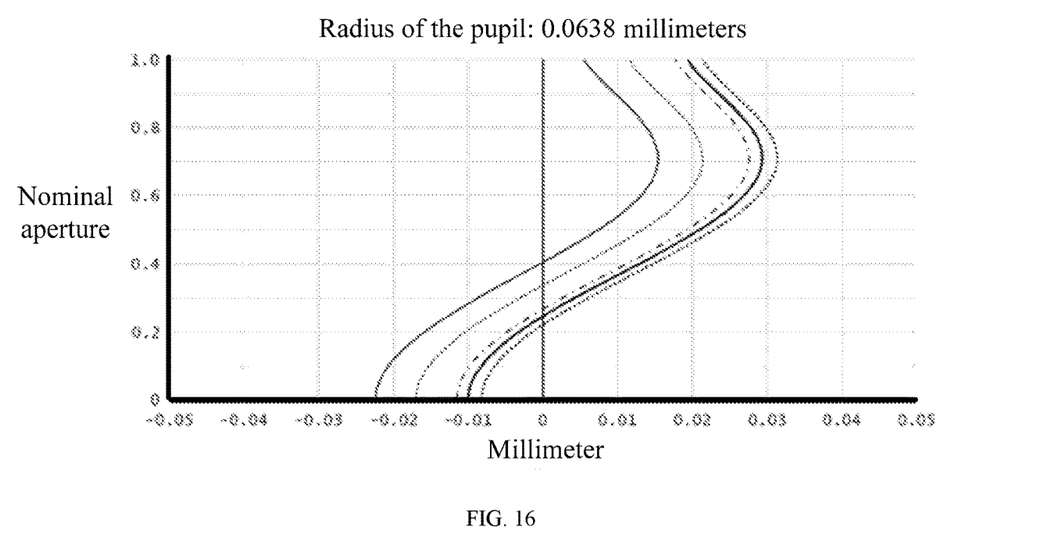
FIG. 16 is a diagram illustrating axial chromatic aberration curves of the endoscope lens provided by the fourth embodiment of the present disclosure.

In this embodiment, the field curvatures, distortions and axial chromatic aberrations thereof are shown in FIG. 14, FIG. 15, and FIG. 16, respectively. It can be seen from FIG. 14 to FIG. 16 that the field curvatures, distortions, and chromatic aberrations can all be well corrected in this embodiment. It should be noted that, there are multiple curves in FIG. 14 and FIG. 16, in which different solid lines or dashed lines correspond to different wavelengths.

Embodiment 5

Figure 17:
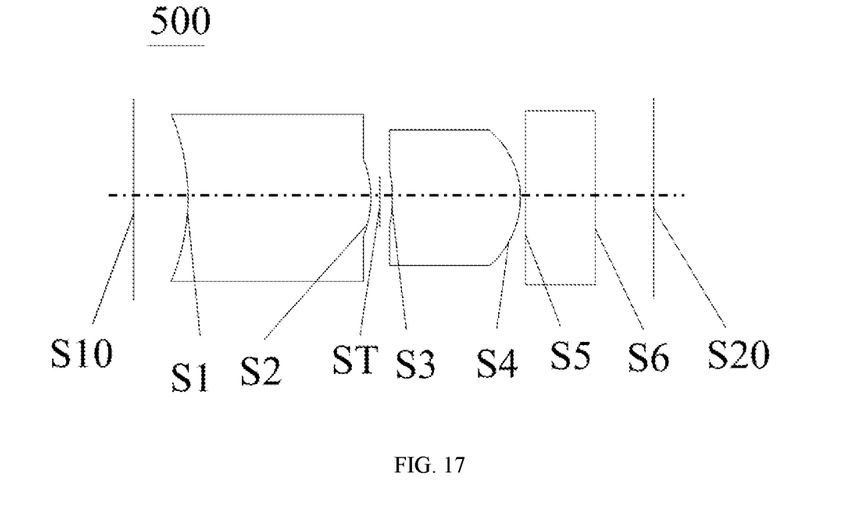
FIG. 17 is a schematic cross-section view illustrating a structure of an endoscope lens provided by a fifth embodiment of the present disclosure.

Referring to FIG. 17, the structure of an endoscope lens 500 provided by a fifth embodiment of the present disclosure is illustrated. The endoscope lens 500 in this embodiment is substantially the same as the endoscope lens 100 in the first embodiment, except that: in this embodiment, the stop ST of the endoscope lens 500 is disposed between the first lens L1 and the second lens L2, and the radius of curvature and material of each lens are selected differently. The specific parameters of the individual lenses are shown in Table 5-1. The diameter of the second lens L2 is smaller than the diameter of the first lens L1.

TABLE 5-1

| Surface No. | Surface type | Radius of curvature | Thickness | Refractive index | Abbe number |
|---|---|---|---|---|---|
| S10 | Object plane | Infinity | 10.000000 | | |
| S1 | Aspheric surface | −0.496826 | 0.549441 | 1.693 | 53.20 |
| S2 | Aspheric surface | −0.276341 | 0.026422 | | |
| ST | Stop | Infinity | 0.037997 | | |
| S3 | Aspheric surface | −0.373511 | 0.385209 | 1.497 | 81.52 |
| S4 | Aspheric surface | −0.188617 | 0.014944 | | |
| S5 | Spherical surface | Infinity | 0.210000 | 1.517 | 64.21 |
| S6 | Spherical surface | Infinity | 0.175035 | | |
| S20 | Image plane | Infinity | — | | |

The parameters of the aspheric surfaces of the individual aspheric lenses in this embodiment are shown in Tables 5-2A and 5-2B.

TABLE 5-2A

| Surface No. | K | B | C |
|---|---|---|---|
| S1 | −0.120811 | 1.045402E+01 | −1.665874E+02 |
| S2 | 0.478608 | 7.825093E+00 | 6.296704E+03 |
| S3 | 2.098571 | −3.317287E+01 | 2.416810E+04 |
| S4 | −0.897731 | 5.263442E+00 | 7.415237E+02 |

TABLE 5-2B

| Surface No. | D | E | F |
|---|---|---|---|
| S1 | 1.173340E+03 | 2.153552E+03 | −6.287724E+04 |
| S2 | −8.521894E+05 | 4.969741E+07 | −1.083374E+09 |
| S3 | −4.643828E+06 | 6.301586E+08 | −3.819206E+10 |
| S4 | −3.165624E+04 | 6.568512E+05 | −5.559424E+06 |

Figure 18:
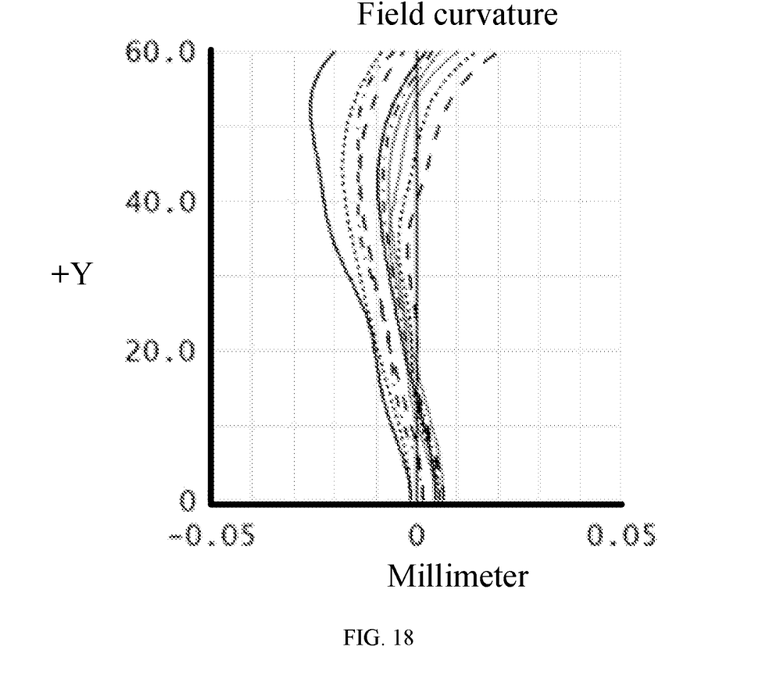
FIG. 18 is a diagram illustrating field curves of the endoscope lens provided by the fifth embodiment of the present disclosure.
Figure 19:
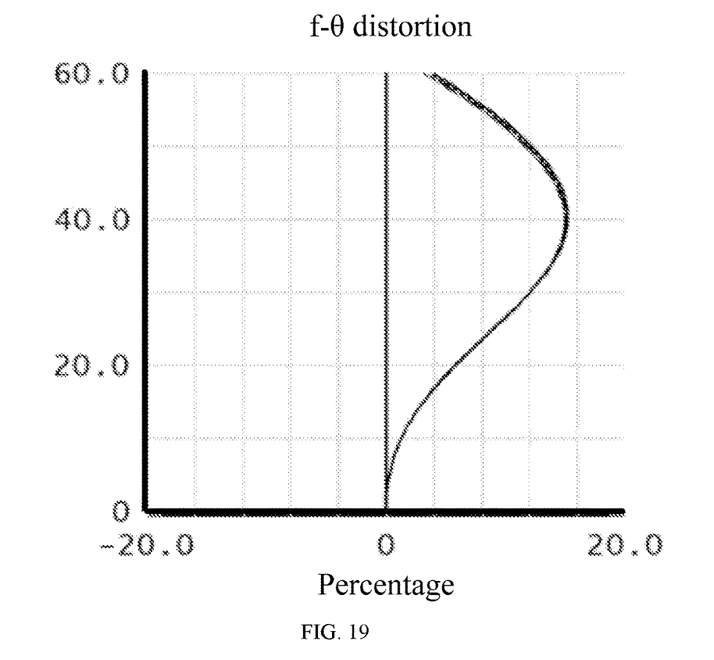
FIG. 19 is a diagram illustrating a distortion curve of the endoscope lens provided by the fifth embodiment of the present disclosure.
Figure 20:
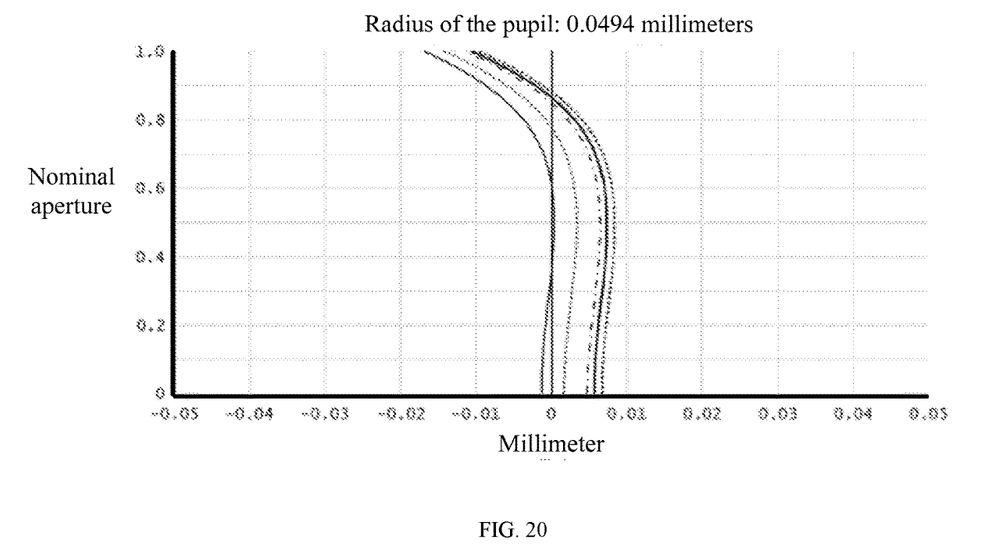
FIG. 20 is a diagram illustrating axial chromatic aberration curves of the endoscope lens provided by the fifth embodiment of the present disclosure.

In this embodiment, the field curvatures, distortions and axial chromatic aberrations thereof are shown in FIG. 18, FIG. 19 and FIG. 20, respectively. It can be seen from FIG. 18 to FIG. 20 that the field curvatures, distortions, and chromatic aberrations can all be well corrected in this embodiment. It should be noted that, there are multiple curves in FIG. 18 and FIG. 20, in which different solid lines or dashed lines correspond to different wavelengths.

Referring to Table 6, the optical characteristics corresponding to the above five embodiments, including the system focal length f, the F number Fno, the field of view 2θ and the optical total length TTL, as well as values corresponding to each of the foregoing expressions are illustrated.

TABLE 6

| Expression | Embodiment 1 | Embodiment 2 | Embodiment 3 | Embodiment 4 | Embodiment 5 |
|---|---|---|---|---|---|
| f (mm) | 0.385 | 0.586 | 0.431 | 0.357 | 0.277 |
| Fno | 2.760 | 2.822 | 2.820 | 3.083 | 2.802 |
| 2θ(deg) | 125.0 | 130.0 | 120.0 | 122.0 | 120.0 |
| TTL(mm) | 1.30 | 1.32 | 1.01 | 1.02 | 1.40 |
| r1/r2 | 15.3 | 5.2 | 4.1 | 1.3 | 1.8 |
| (f$^2$/Fno) + f | 0.439 | 0.708 | 0.497 | 0.399 | 0.304 |
| TTL/D$_{max}$ | 1.506 | 1.281 | 1.522 | 2.943 | 2.785 |
| IH/θ | 0.0075 | 0.008 | 0.007 | 0.005 | 0.006 |

All of the foregoing embodiments achieve the following optical indexes: (1) the field of view: 2θ ≥120°: (2) the optical total length: TTL<1.50 mm: and (3) the applicable spectral range: 400 nm-700 nm.

In the endoscopic lens provided by the embodiments of the present disclosure, the first lens L1 is configured to collect light and correct distortions, and enables the diameter of the endoscope lens to be effectively reduced. The second lens L2 is mainly configured to eliminate aberrations, such as spherical aberration, field curvature, and astigmatism.

Embodiment 6

Figure 21:
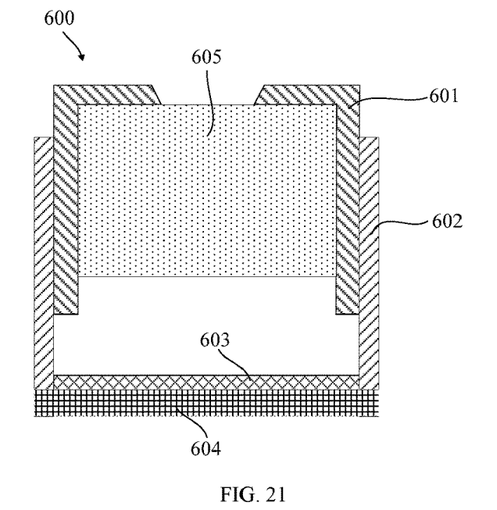
FIG. 21 is a schematic structural diagram showing a cross-section of a camera module provided by a sixth embodiment of the disclosure.

Referring to FIG. 21, a cross-section of a camera module 600 provided by this embodiment is illustrated. The camera module 600 includes a barrel 601, a holder 602, an image sensor 603, a printed circuit board 604, and an endoscope lens 605 provided by any of the embodiments as described above. The endoscope lens 605 is received in the barrel 601, and the barrel 601 is engaged with the holder 602. The image sensor 603 is substantially accommodated in the holder 602, and the printed circuit board 604 is attached to the holder 602. The image sensor 603 is opposite to the endoscope lens 605 and is mounted on the printed circuit board 604. The image sensor 603 is configured to convert light signal into electrical signals, thereby the images formed by the endoscope lens 605 can be converted and transmitted to a processor. The printed circuit board 604 can be further electrically connected to a chip or the processor via a flexible circuit board.

Embodiment 7

Figure 22:
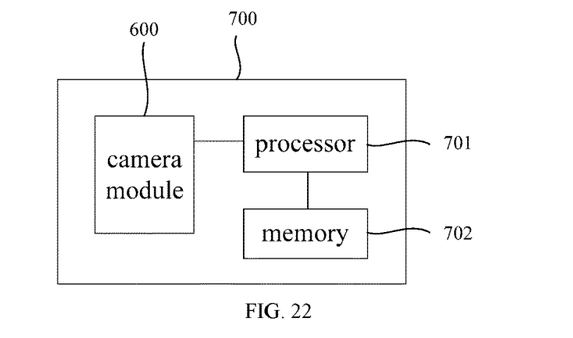
FIG. 22 is a schematic block diagram of an endoscope camera to be applied to an endoscope provided by a seventh embodiment of the disclosure.
Figure 23:
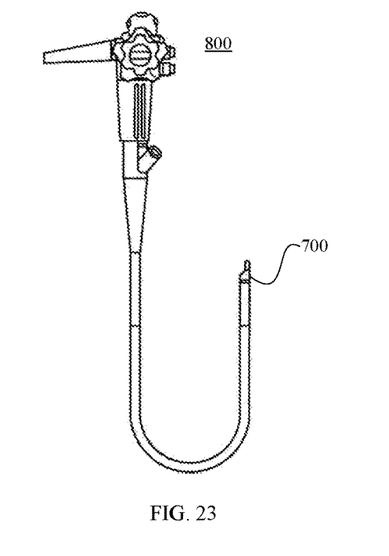
FIG. 23 is a schematic diagram of the endoscope provided by the seventh embodiment of the disclosure.

FIGS. 22 and 23 schematically illustrates an endoscope camera 700 applied to an endoscope 800. The endoscope camera 700 includes the camera module 600 as described above, a processor 701, and a memory 702. The camera module 600 is configured to capture images, the processor 701 is configured to process the captured images, and the memory 702 is configured to store the captured images. The processor 701 is communicated with the camera module 600 and the memory 702. That is, the electrical signals of the images can be transmitted to the processor 701 and stored in the memory 702. When the endoscope 800 in particular the endoscope camera 700 thereof is placed into the human body, physical examination can be executed based on the captured images of camera module 600.

In summary, in the endoscope lens provided by the embodiments of the present disclosure, by means of the reasonable arrangement and coordination of the individual lenses, the filter and the stop, the diameter of the endoscope lens can be reduced while ensuring a wide field of view. The diameter of the endoscope lens can be reduced to be no more than 1.0 mm, and the optical total length of the endoscope lens can be less than or equal to 2.0 mm. This can effectively relieve the patient's pain during physical examination, and can enable the endoscope lens to access a narrow lesion part for examination. Further, the field of view of the endoscope lens can be ensured to be greater than or equal to 120°, and a clear image can be obtained within a range of depth of field from 5 mm to 35 mm. This enables the endoscope lens to have a small diameter, an extended depth of field, and a wide field of view, effectively increasing the observed range and the observed depth. In addition, the endoscope lens also has small distortion, which improves the resolving power at the edge and ensures the imaging effect.

The above-mentioned embodiments only illustrate several implementations of the present disclosure, and the description thereof is relatively exhaustive, but they should not be understood as limiting the protection scope of the present disclosure. It should be noted that, for those of ordinary skill in the art, several modifications and improvements can be made without departing from the concept of the present disclosure, and they should all fall within the protection scope of the present disclosure. Therefore, the protection scope of the present disclosure should be subject to the appended claims.

What is claimed is:

1. An endoscope lens, from an object side to an image side thereof, the endoscope lens consisting of following components sequentially:
   a stop;
   a first lens having a concave object side surface and a convex image side surface;
   a second lens; and
   a filter arranged between the second lens and the image side;
   wherein the first lens is a glass or plastic aspheric lens, and the second lens is a glass or plastic aspheric lens;
   wherein the endoscope lens meets an expression:

$0<(f^2/Fno)+f<1;$ where f represents an effective focal length of the endoscope lens, and Fno represents an F number of the endoscope lens; and
   wherein a field of view of the endoscope lens is greater than or equal to 120°, and an optical total length of the endoscope lens is less than 1.50 mm.

2. The endoscope lens as claimed in claim 1, wherein the endoscope lens meets expressions:

$r1/r2>1;$ $TTL/D_{max}<3;$ where r1 represents a radius of curvature of the object side surface of the first lens, r2 represents a radius of curvature of the image side surface of the first lens, TTL represents the optical total length of the endoscope lens, and $D_{max}$ represents a diameter of a largest one of the lenses in the endoscope lens.

3. The endoscope lens as claimed in claim 1, wherein an object side surface of the second lens comprises a central concave portion and a flat portion surrounds the concave portion.

4. The endoscope lens as claimed in claim 1, wherein the endoscope lens meets an expression:

$0 \text{ mm}/°<IH/θ<0.01 \text{ mm}/°;$ where θ represents half of the field of view of the endoscope lens, and IH represents an actual image height of the endoscope lens at the half of the field of view θ.

5. The endoscope lens as claimed in claim 2, wherein the radius of curvature of the object side surface of the first lens has a same sign as the radius of curvature of the image side surface of the first lens.

6. The endoscope lens as claimed in claim 1, wherein a surface shape of each of the aspheric lenses of the endoscope lens meets an expression:

$$z = \frac{ch^2}{1+\sqrt{1-(1+K)c^2h^2}} + Bh^4 + Ch^6 + Dh^8 + Eh^{10} + Fh^{12};$$

where z represents a distance between a point on a curved surface and a vertex of the curved surface along an optical axis, c represents a curvature of the vertex of the curved surface, K represents a quadratic surface coefficient, h represents a distance between the point on the curved surface and the optical axis, B represents a fourth order surface coefficient, C represents a sixth order surface coefficient, D represents an eighth order surface coefficient, E represents a tenth order surface coefficient, and F represents a twelfth order surface coefficient.

7. The endoscope lens as claimed in claim 1, wherein a diameter of the first lens is smaller than a diameter of the second lens.

8. The endoscope lens as claimed in claim 1, wherein the first lens is a meniscus lens.

9. The endoscope lens as claimed in claim 1, wherein a diameter of the stop is smaller than a diameter of the first lens, and smaller than a diameter of the second lens.

10. The endoscope lens as claimed in claim 1, wherein an object side surface of the second lens is concave, and an image side surface of the second lens is convex.

11. The endoscope lens as claimed in claim 1, wherein an object side surface and an image side surface of the second lens are both convex.

12. The endoscope lens as claimed in claim 1, wherein a center thickness of the first lens is larger than a center thickness of the second lens.

13. The endoscope lens as claimed in claim 1, wherein a distance between the second lens and the filter is smaller than the distance between the filter and an image plane, along an optical axis of the endoscope lens.

14. A camera module, comprising an endoscope lens and an image sensor opposite to the endoscope lens, wherein from an object side to an image side, the endoscope lens consisting of following components sequentially:
a first lens having a concave object side surface and a convex image side surface;
a stop;
a second lens; and
a filter arranged between the second lens and the image side; wherein each of the first lens and the second lens is an aspheric lens;
wherein the endoscope lens meets expressions:

$r1/r2>1;$ $TTL/D_{max}<3;$ $0<(f^2/Fno)+f<1;$ where r1 represents a radius of curvature of the object side surface of the first lens, r2 represents a radius of curvature of the image side surface of the first lens, TTL represents an optical total length of the endoscope lens, $D_{max}$ represents a diameter of the largest one of the lenses in the endoscope lens, f represents an effective focal length of the endoscope lens, and Fno represents an F number of the endoscope lens; and
wherein a field of view of the endoscope lens is greater than or equal to 120°, and the optical total length of the endoscope lens is less than 1.50 mm.

15. The camera module as claimed in claim 14, wherein the endoscope lens meets an expression:

$0 \text{ mm}/° < IH/\theta < 0.01 \text{ mm}/°;$ where θ represents half of the field of view of the endoscope lens, and IH represents an actual image height of the endoscope lens at the half of the field of view θ.

16. An endoscope, comprising an camera module, a processor and a memory, wherein the camera module is configured to capture one or more images, the processor is configured to process the captured one or more images, and the memory is configured to store the one or more images; the camera module comprises an endoscope lens and an image sensor opposite to the endoscope lens, and from an object side to an imaging surface of the endoscope lens, the endoscope lens consisting of following components sequentially:
a first lens having a concave object side surface and a convex image side surface;
a stop;
a second lens; and
a filter arranged between the second lens and the image side;
wherein each of the first lens and the second lens is an aspheric lens;
wherein the endoscope lens meets an expression:

$0<(f^2/Fno)+f<1;$ where f represents an effective focal length of the endoscope lens, and Fno represents an F number of the endoscope lens; and
wherein a field of view of the endoscope lens is greater than or equal to 120°, and an optical total length of the endoscope lens is less than 1.50 mm.

17. The endoscope as claimed in claim 16, wherein a radius of curvature of the object side surface of the first lens has a same sign as a radius of curvature of the image side surface of the first lens.

* * * * *